US005939064A

United States Patent [19]
Savelkoul et al.

[11] Patent Number: 5,939,064

[45] Date of Patent: Aug. 17, 1999

[54] *BORDETELLA BRONCHISEPTICA* VACCINE

[75] Inventors: Paul Savelkoul; Willem Gaastra, both of Weesp, Netherlands

[73] Assignee: American Cyanamid Company, Madison, N.J.

[21] Appl. No.: 08/381,881

[22] PCT Filed: Jul. 28, 1993

[86] PCT No.: PCT/NL93/00161

§ 371 Date: Apr. 19, 1995

§ 102(e) Date: Apr. 19, 1995

[87] PCT Pub. No.: WO94/04683

PCT Pub. Date: Mar. 3, 1994

[30] Foreign Application Priority Data

Aug. 18, 1992 [EP] European Pat. Off. .............. 92202525

[51] Int. Cl.$^6$ .............................................. A61K 48/00

[52] U.S. Cl. .......................... 424/93.2; 514/44; 536/23.1; 435/320.1; 435/69.1; 435/455

[58] Field of Search ............................... 424/93.2, 178.1, 424/184.1, 190.1; 530/387.3; 435/69.1, 172.3, 326.1, 455; 935/52, 55, 72; 514/44; 536/23.1

[56] References Cited

U.S. PATENT DOCUMENTS 4,920,048 4/1990 Diderichsen .......................... 435/69.1

FOREIGN PATENT DOCUMENTS 0141671 5/1985 European Pat. Off. .
0324124 7/1989 European Pat. Off. .
0419997 4/1991 European Pat. Off. .

OTHER PUBLICATIONS

Immunology, vol. 78, No. 6, pp. 3824–3828, Jun. 1981, *Proc. Natl. Acad. Sci.*, USA, "Prediction of protein antigenic determinants from amino acid sequences", Thomas P. Hopp et al.

*Advances in Immunology*, 47, pp. 45–148, Peter Y. Chou et al., "Prediction of the Secondary Structure of Protein from their Amino Acid Sequence".

*Naturwissenschaften* 72 (1985), P.A. Karplus, et al., "Prediction of Chain Flexibility in Proteins: A Tool for the Selection of Peptide Antigens".

*Biophys. J.*, Biophysical Society, vol. 26, Jun. 1979, pp. 367–384, Peter Y. Chou et al., "Prediction of β–Turns".

*CABIOS*, vol. 4, No. 3, 1988, pp. 357–365, O. Gascuel et al., "A simple method for predicting the secondary structure of globular proteins: implications and accuracy".

*Nucleic Acids Research*, vol. 12, No. 1, 1984, pp. 243–255, Jiři Novotny et al., "A program for prediction of protein secondary structure from nucleotide sequence data: application to histocompatibility antigens".

*Proc. Natl. Acad. Sci.*, vol. 81, Jul. 1984, pp. 3998–4002, H. Mario Geysen et al., "Use of peptide synthesis to probe viral antigens for epitopes to a resolution of a single amino acid".

*The EMBO Journal*, vol. 3, No. 6, 1984, pp. 1429–1434, Keith K. Stanley et al., "Construction of a new family of high efficiency bacterial expression vectors: identification of cDNA clones coding for human liver proteins".

*The Journal of Immunology*, vol. 143, No. 8, Oct. 15, 1989, pp. 2692–2698, Johannes G. Kusters et al., "Analysis of an Immunodominant Region of Infectious Bronchitis Virus".

*Microbial Pathogenesis*, vol. 2, 1987, pp. 473–484, Frits R. Mooi et al., "Characterization of fimbrial subunits from Bordetella species".

*Abstracts of General Meeting of Am. Soc. Microbiol.*, vol. 92, p. 193, Eugene H. Burns, Jr., "Comparison of Fimbrial Serotype 2 Subunit Antigen Expression Levels in *Bordetella bronchiseptica* Strains".

*Molecular Microbiology*, vol. 2, No. 4, 1988, pp. 539–543, P. Pendroni et al., "Cloning of a novel pilin–like gene from *Bordetella pertussis*: homology to the fim2 gene".

*Nucleic Acids Research*, vol. 17, No. 19, 1989, p. 8007, Johannes G. Kusters et al., "Improvements of the cloning linker of the bacterial expression vector pEX".

*Molecular Microbiology*, vol. 1, No. 2, 1987, pp. 203–209, I. Livey et al., "Cloning and nucleotide sequence analysis of the serotype 2 fimbrial subunit gene of *Bordetella pertussis*".

Ngo et al., The Protein Folding Problem and Tertiary Prediction, 1994, Merz et al. (ed.), Birkhauser, Boston, MA, pp. 492–495.

Makela et al. (1996) Vaccine, vol. 14, No. 7: 719–732.

Robert Whalen (1996) Emerging Infectious Diseases, vol. 2, No. 3:168–175.

Etlinger (1992) Immunology Today, vol. 13, No. 2: 52–55.

Glick et al. (1994) Molecular Biotechnology, ASM Press:214.

Burns et al. (1993) J. Clin. Microb., vol. 31, No. 7: 1838–1844.

*Primary Examiner*—Bruce R. Campell
*Assistant Examiner*—Dave Trong Nguyen
*Attorney, Agent, or Firm*—Stevens, Davis, Miller & Mosher, L.L.P.

[57] ABSTRACT

The present invention is concerned with a vaccine for combating *B. bronchiseptica* infection in susceptible animals (such as dogs and swine), containing proteins or polypeptides typical of the fimbrial protein of *B. bronchiseptica,* or containing recombinant polynucleotides having as part thereof a polynucleotide coding for said protein or polypeptide, and also is concerned with the preparation of said proteins, polypeptides and polynucleotides.

5 Claims, 4 Drawing Sheets

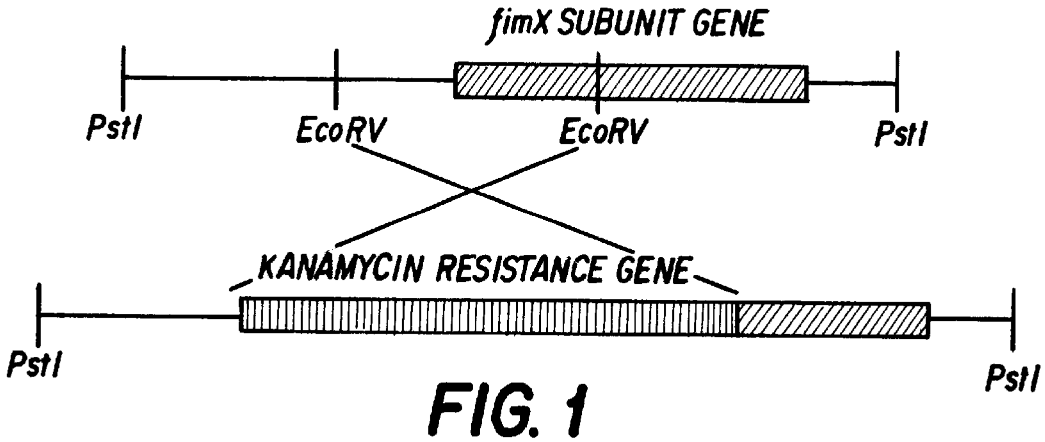
FIG. 1
FIG. 2
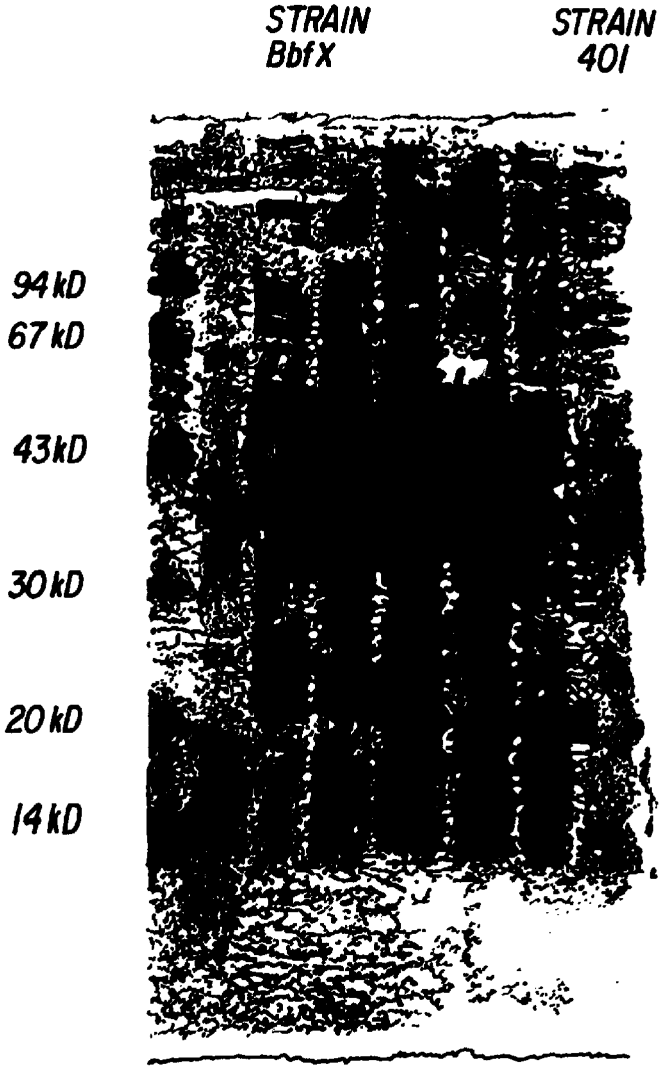

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
(A) LENGTH: 1315 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Bordetella bronchiseptica
(B) STRAIN: 401

(vii) IMMEDIATE SOURCE:
(B) CLONE: E coli PC2495(pIVB3-420)

(ix) FEATURE:
(A) NAME/KEY: misc_feature
(B) LOCATION: 1..539

(ix) FEATURE:
(A) NAME/KEY: CDS
(B) LOCATION: 540..1142

(ix) FEATURE:
(A) NAME/KEY: misc_feature
(B) LOCATION: 1143..1315

(xi) SEQUENCE DESCRIPTION: SEQ ID NO:1:

```
CTGCAGGTCA ACGGATCCAG TATTCGTCGA GCGATCCCAA GACCCAGACG GCGCAGATCT     60

CCGGCGCGAC CGAGACCACC GGCGTGCAGA TACGCCTGTC CAACCTGAAC GACAGCAAGA    120

TCACCATGGG CGCGAACGAG CAGATGCAGC ACGCACAGGG CTTCGACCCG GTCGCCCAGG    180

CATCGGGCGG CAAGAAGAGC GTGACCCTGA GCTACCTTGC TTCGTATGTG CGCAAGAGCA    240

GCGGCCGACG TGGACAGCGG CTCGATTACC ACCTACGTGG CTTCTCTGTG GTCTACCCCT    300

AGCGGGGCGA ATGCAGCGGA TATCGACGTC AGCTTGGGCC AAATCCTATA GGATGACGAA    360

CAAGCCTCTC GATGGCGGGC CGATTGCTTA CCACGTAAGT GGTTCCCGCC GTCGTCTGTG    420

CCTGATATGG CGAAGGCGGG CCAAATTCCT AGATACCCAT GAGGCCCCCC CCCCCCCCTG    480

AGGCGTCCAA TAATCTTGCA CACACATTGT CCCTGGATCC CTTCTTTACT CCAGCCTGT     539

ATG CAA GCC AAA ACG TTC CTC CTG GGC GCG GCG CTC GCC GGC GTC GCG      587
Met Gln Ala Lys Thr Phe Leu Leu Gly Ala Ala Leu Ala Gly Val Ala
  1               5                  10                  15

CTC GCC GCC CAT GCC GAA GAC GGC ACC ATT GTC ATT ACC GGC ACG ATC      635
Leu Ala Ala His Ala Glu Asp Gly Thr Ile Val Ile Thr Gly Thr Ile
             20                  25                  30

ACC GAC CAG ACC TGC ACG ATC GAG GAC CCG AGC CCC GGT TAC ATC AAG      683
Thr Asp Gln Thr Cys Thr Ile Glu Asp Pro Ser Pro Gly Tyr Ile Lys
         35                  40                  45

GTC GTG CAC CTG CCC ACG ATC TCC AAG AGC GCG CTG AAG AAC GCC GGC      731
Val Val His Leu Pro Thr Ile Ser Lys Ser Ala Leu Lys Asn Ala Gly
     50                  55                  60

GAC GTG GCG GGG CGC ACT CGC TTC GAT ATC AAG CTG AAG GAC TGC CCG      779
Asp Val Ala Gly Arg Thr Arg Phe Asp Ile Lys Leu Lys Asp Cys Pro
 65                  70                  75                  80
```

-continued

```
ACC ACC GTC AAC ACT CTC AAG CTG TAC TTC GAG CCC GGC CCC ACC ACG      827
Thr Thr Val Asn Thr Leu Lys Leu Tyr Phe Glu Pro Gly Pro Thr Thr
                 85                  90                  95

GAT TAC GGC ACC AAG GAT CTG AAA GCC TAT AAG CAG GCT TGG TAC GTC      875
Asp Tyr Gly Thr Lys Asp Leu Lys Ala Tyr Lys Gln Ala Trp Tyr Val
            100                 105                 110

GAC GCC GCA ACG CTG CTC AAA TCG CCG CCC AGT GTG ACC GAA GCC AAG      923
Asp Ala Ala Thr Leu Leu Lys Ser Pro Pro Ser Val Thr Glu Ala Lys
        115                 120                 125

GGG GTG CAG ATC CGG CTG ATG AAC CTG AAC GGC AAG CAG ATT CCC ATG      971
Gly Val Gln Ile Arg Leu Met Asn Leu Asn Gly Lys Gln Ile Pro Met
    130                 135                 140

GGC GAG ACC GAG CCC AAC CAG CAT GCC GCG GCA TTT TCC GGC ACC ATG     1019
Gly Glu Thr Glu Pro Asn Gln His Ala Ala Ala Phe Ser Gly Thr Met
145                 150                 155                 160

CAA GCC GGC CAG GCG AAG AAA TCG TTC ACC TTG CAC TAC CTG GCC GGC     1067
Gln Ala Gly Gln Ala Lys Lys Ser Phe Thr Leu His Tyr Leu Ala Gly
                165                 170                 175

TAC GTG AAG AAG GCC AGT GGA GAG GTC GAG GCG ACC ATG CTG ACC ACC     1115
Tyr Val Lys Lys Ala Ser Gly Glu Val Glu Ala Thr Met Leu Thr Thr
            180                 185                 190

TAC GTG GGC TTT TCG GTC GTC TAC CCC TGAAACGCAC AGGCCATGGC           1162
Tyr Val Gly Phe Ser Val Val Tyr Pro
        195                 200

GGCCGGCGTT GCGCCCTGCG AACCCCGGCG ATCAGCGCGG CCGCTTGTCG ATGACGCGCC   1222

GCGCCTTGCC CGTCAGGGTA CGCTCGACGA AGCCCGTGTC GGCAACCTGC ACGCGGGCGT   1282

GACGCCGATG TATGACTTGA CCGCATGCTG CAG                                1315
```

(2) INFORMATION FOR SEQ ID NO:2:

(i) SEQUENCE CHARACTERISTICS:
(A) LENGTH: 201 amino acids
(B) TYPE: amino acid
(D) TOPOLOGY: linear (ii) MOLECULE TYPE: protein (xi) SEQUENCE DESCRIPTION: SEQ ID NO:2:

```
Met Gln Ala Lys Thr Phe Leu Leu Gly Ala Ala Leu Ala Gly Val Ala
  1               5                  10                  15

Leu Ala Ala His Ala Glu Asp Gly Thr Ile Val Ile Thr Gly Thr Ile
             20                  25                  30

Thr Asp Gln Thr Cys Thr Ile Glu Asp Pro Ser Pro Gly Tyr Ile Lys
         35                  40                  45

Val Val His Leu Pro Thr Ile Ser Lys Ser Ala Leu Lys Asn Ala Gly
     50                  55                  60

Asp Val Ala Gly Arg Thr Arg Phe Asp Ile Lys Leu Lys Asp Cys Pro
 65                  70                  75                  80

Thr Thr Val Asn Thr Leu Lys Leu Tyr Phe Glu Pro Gly Pro Thr Thr
                 85                  90                  95

Asp Tyr Gly Thr Lys Asp Leu Lys Ala Tyr Lys Gln Ala Trp Tyr Val
            100                 105                 110

Asp Ala Ala Thr Leu Leu Lys Ser Pro Pro Ser Val Thr Glu Ala Lys
        115                 120                 125

Gly Val Gln Ile Arg Leu Met Asn Leu Asn Gly Lys Gln Ile Pro Met
    130                 135                 140

Gly Glu Thr Glu Pro Asn Gln His Ala Ala Ala Phe Ser Gly Thr Met
145                 150                 155                 160
```

```
Gln Ala Gly Gln Ala Lys Lys Ser Phe Thr Leu His Tyr Leu Ala Gly
            165                 170                 175

Tyr Val Lys Lys Ala Ser Gly Glu Val Glu Ala Thr Met Leu Thr Thr
            180                 185                 190

Tyr Val Gly Phe Ser Val Val Tyr Pro
        195                 200
```

(2) INFORMATION FOR SEQ ID NO:3:

(i) SEQUENCE CHARACTERISTICS:
(A) LENGTH: 624 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Bordetella bronchiseptica
(B) STRAIN: 401

(vii) IMMEDIATE SOURCE:
(B) CLONE: E coli PC2495(pIVB3-402)

(ix) FEATURE:
(A) NAME/KEY: CDS
(B) LOCATION: 1..624

(xi) SEQUENCE DESCRIPTION: SEQ ID NO:3:

```
ATG CAA GTC CCT TTC CAA CGC GCC CTG CCG CTG TGC TTG CGG GCC GCT       48
Met Gln Val Pro Phe Gln Arg Ala Leu Pro Leu Cys Leu Arg Ala Ala
  1               5                  10                  15

CTG GCG GCC ATT GCG TCC GCG GCG CAC GCC GAC GAC GGC ACC ATC GTC       96
Leu Ala Ala Ile Ala Ser Ala Ala His Ala Asp Asp Gly Thr Ile Val
             20                  25                  30

ATC ACC GGC ACC ATC ACC GAC ACC ACC TGC GTC ATC GAG GAC CCG GCC      144
Ile Thr Gly Thr Ile Thr Asp Thr Thr Cys Val Ile Glu Asp Pro Ala
         35                  40                  45

GGC CCC ACG CAC ACC AAG GTG GTG CAA TTG CCC AAG ATA TCC AAG AGC      192
Gly Pro Thr His Thr Lys Val Val Gln Leu Pro Lys Ile Ser Lys Ser
     50                  55                  60

GCG CTG GCC AAG GAT GGA GAC GAA GCT GGC CGT ACG CCC TTC CTG ATC      240
Ala Leu Ala Lys Asp Gly Asp Glu Ala Gly Arg Thr Pro Phe Leu Ile
 65                  70                  75                  80

ACG CTC AAG GAC TGC CCC TCG TCC CTG AAC AAT GGC GTG AAA GCG TAC      288
Thr Leu Lys Asp Cys Pro Ser Ser Leu Asn Asn Gly Val Lys Ala Tyr
                 85                  90                  95

TTC GAG CCT GGG CCG ACC ACC GAC TAC GCT ACC GGC GAC CTA AAG GCG      336
Phe Glu Pro Gly Pro Thr Thr Asp Tyr Ala Thr Gly Asp Leu Lys Ala
            100                 105                 110

TAT TCG ATC GCC TAC AAC AAC AAC CCC GCC ACC ACC CAA AAT GCG ATC      384
Tyr Ser Ile Ala Tyr Asn Asn Asn Pro Ala Thr Thr Gln Asn Ala Ile
        115                 120                 125

ATC GCT GCA AGC GAA GCG CAG GGC GTG CAA ATC CGC ATC TCC AAC CAG      432
Ile Ala Ala Ser Glu Ala Gln Gly Val Gln Ile Arg Ile Ser Asn Gln
    130                 135                 140

AAC GGC ACC AAG ATC CCC ATG GGC GTG GAC GCC GCC GCC CAG AAC GCC      480
Asn Gly Thr Lys Ile Pro Met Gly Val Asp Ala Ala Ala Gln Asn Ala
145                 150                 155                 160

CAG GCC TTC AAC CCC GTC ACC GAC ACC GCC GAC AAC GCC AAG AAG AAG      528
Gln Ala Phe Asn Pro Val Thr Asp Thr Ala Asp Asn Ala Lys Lys Lys
```

-continued

```
                165                 170                 175

GTC ACG TTG CGC TAC CTG GCA TCG TAC GTA AAG AAA TCC GGC AAC ATT      576
Val Thr Leu Arg Tyr Leu Ala Ser Tyr Val Lys Lys Ser Gly Asn Ile
            180                 185                 190

ACT GCC GGG CAA CTC ACG ACA TAC GTC GGT TTT TCC ATG ATC TAT CCG      624
Thr Ala Gly Gln Leu Thr Thr Tyr Val Gly Phe Ser Met Ile Tyr Pro
        195                 200                 205
```

(2) INFORMATION FOR SEQ ID NO:4:

(i) SEQUENCE CHARACTERISTICS:
(A) LENGTH: 208 amino acids
(B) TYPE: amino acid
(D) TOPOLOGY: linear (ii) MOLECULE TYPE: protein (xi) SEQUENCE DESCRIPTION: SEQ ID NO:4:

```
Met Gln Val Pro Phe Gln Arg Ala Leu Pro Leu Cys Leu Arg Ala Ala
  1               5                  10                  15

Leu Ala Ala Ile Ala Ser Ala Ala His Ala Asp Asp Gly Thr Ile Val
             20                  25                  30

Ile Thr Gly Thr Ile Thr Asp Thr Thr Cys Val Ile Glu Asp Pro Ala
         35                  40                  45

Gly Pro Thr His Thr Lys Val Val Gln Leu Pro Lys Ile Ser Lys Ser
     50                  55                  60

Ala Leu Ala Lys Asp Gly Asp Glu Ala Gly Arg Thr Pro Phe Leu Ile
 65                  70                  75                  80

Thr Leu Lys Asp Cys Pro Ser Ser Leu Asn Asn Gly Val Lys Ala Tyr
                 85                  90                  95

Phe Glu Pro Gly Pro Thr Thr Asp Tyr Ala Thr Gly Asp Leu Lys Ala
            100                 105                 110

Tyr Ser Ile Ala Tyr Asn Asn Asn Pro Ala Thr Thr Gln Asn Ala Ile
        115                 120                 125

Ile Ala Ala Ser Glu Ala Gln Gly Val Gln Ile Arg Ile Ser Asn Gln
    130                 135                 140

Asn Gly Thr Lys Ile Pro Met Gly Val Asp Ala Ala Ala Gln Asn Ala
145                 150                 155                 160

Gln Ala Phe Asn Pro Val Thr Asp Thr Ala Asp Asn Ala Lys Lys Lys
                165                 170                 175

Val Thr Leu Arg Tyr Leu Ala Ser Tyr Val Lys Lys Ser Gly Asn Ile
            180                 185                 190

Thr Ala Gly Gln Leu Thr Thr Tyr Val Gly Phe Ser Met Ile Tyr Pro
        195                 200                 205
```

(2) INFORMATION FOR SEQ ID NO:5:

(i) SEQUENCE CHARACTERISTICS:
(A) LENGTH: 621 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Bordetella bronchiseptica
(B) STRAIN: 401

(vii) IMMEDIATE SOURCE:
          (B) CLONE: E coli PC2495(pIVB3-430)

(ix) FEATURE:
          (A) NAME/KEY: CDS
          (B) LOCATION: 1..621

(xi) SEQUENCE DESCRIPTION: SEQ ID NO:5:

```
ATG TCC AAG TTT TCA TAC CCC GCC TTG CGC ACC GCG CTT ATC CTT GCC        48
Met Ser Lys Phe Ser Tyr Pro Ala Leu Arg Thr Ala Leu Ile Leu Ala
  1               5                  10                  15

GCC TCG CCC GTG CTG CCG GCG CAT GCC AAC GAT GGC ACC ATC GTC ATC        96
Ala Ser Pro Val Leu Pro Ala His Ala Asn Asp Gly Thr Ile Val Ile
             20                  25                  30

ACC GGC AGC ATC TCC GAC CAG ACC TGC GTC ATC GAA GAG CCC AGC GCC       144
Thr Gly Ser Ile Ser Asp Gln Thr Cys Val Ile Glu Glu Pro Ser Ala
         35                  40                  45

CCC AAC CAT ATC AAG GTC GTG CAA CTG CCC AAG ATT TCC AAG AAC GCG       192
Pro Asn His Ile Lys Val Val Gln Leu Pro Lys Ile Ser Lys Asn Ala
     50                  55                  60

CTC AGG AAC GAC GGC GAC ACC GCC GGC GCC ACG CCC TTC GAC ATC AGG       240
Leu Arg Asn Asp Gly Asp Thr Ala Gly Ala Thr Pro Phe Asp Ile Arg
 65                  70                  75                  80

CTG AAG GAA TGC CCC CAG CTG GGC GCG CTC AAG CTG TAT TTC GAG CCC       288
Leu Lys Glu Cys Pro Gln Leu Gly Ala Leu Lys Leu Tyr Phe Glu Pro
                 85                  90                  95

GGC ATC ACC ACC AAC TAC GAC ACC GGC GAT CTG ATC GCC TAC AAG CAG       336
Gly Ile Thr Thr Asn Tyr Asp Thr Gly Asp Leu Ile Ala Tyr Lys Gln
            100                 105                 110

GCC TAC AAC GCA TCC GGC AAC GGC AAC CTG AGC ACC GTG TCG TCC GCC       384
Ala Tyr Asn Ala Ser Gly Asn Gly Asn Leu Ser Thr Val Ser Ser Ala
        115                 120                 125

ACC AAG GCC AAG GGC GTG GAA TTC CGC CTG GCC AAC CTC AAC GGC CAG       432
Thr Lys Ala Lys Gly Val Glu Phe Arg Leu Ala Asn Leu Asn Gly Gln
    130                 135                 140

CAC ATC CGC ATG GGC ACC GAC GAA ACC ACG CAA GCC GCG CAA ACC TTC       480
His Ile Arg Met Gly Thr Asp Glu Thr Thr Gln Ala Ala Gln Thr Phe
145                 150                 155                 160

ACG GGC ACT GAT GTC ACC AAC GGC GGC AAC ACC ACC AAA AGC TAT ACC       528
Thr Gly Thr Asp Val Thr Asn Gly Gly Asn Thr Thr Lys Ser Tyr Thr
                165                 170                 175

CTG CGC TAT CTC GCC TCG TAC GTG AAG AAA CCC AAC GAA GAT GTC GAC       576
Leu Arg Tyr Leu Ala Ser Tyr Val Lys Lys Pro Asn Glu Asp Val Asp
            180                 185                 190

GCG GCG CAG ATG ACC AGC TAC GTC GGC TTT TCC GTC GTC TAT CCC           621
Ala Ala Gln Met Thr Ser Tyr Val Gly Phe Ser Val Val Tyr Pro
        195                 200                 205
```

(2) INFORMATION FOR SEQ ID NO:6:

(i) SEQUENCE CHARACTERISTICS:
          (A) LENGTH: 207 amino acids
          (B) TYPE: amino acid
          (D) TOPOLOGY: linear (ii) MOLECULE TYPE: protein (xi) SEQUENCE DESCRIPTION: SEQ ID NO:6:

```
Met Ser Lys Phe Ser Tyr Pro Ala Leu Arg Thr Ala Leu Ile Leu Ala
  1               5                  10                  15

Ala Ser Pro Val Leu Pro Ala His Ala Asn Asp Gly Thr Ile Val Ile
             20                  25                  30

Thr Gly Ser Ile Ser Asp Gln Thr Cys Val Ile Glu Glu Pro Ser Ala
```

-continued

```
        35                  40                  45

Pro Asn His Ile Lys Val Val Gln Leu Pro Lys Ile Ser Lys Asn Ala
    50                  55                  60

Leu Arg Asn Asp Gly Asp Thr Ala Gly Ala Thr Pro Phe Asp Ile Arg
65                  70                  75                  80

Leu Lys Glu Cys Pro Gln Leu Gly Ala Leu Lys Leu Tyr Phe Glu Pro
                85                  90                  95

Gly Ile Thr Thr Asn Tyr Asp Thr Gly Asp Leu Ile Ala Tyr Lys Gln
            100                 105                 110

Ala Tyr Asn Ala Ser Gly Asn Gly Asn Leu Ser Thr Val Ser Ser Ala
        115                 120                 125

Thr Lys Ala Lys Gly Val Glu Phe Arg Leu Ala Asn Leu Asn Gly Gln
    130                 135                 140

His Ile Arg Met Gly Thr Asp Glu Thr Thr Gln Ala Ala Gln Thr Phe
145                 150                 155                 160

Thr Gly Thr Asp Val Thr Asn Gly Gly Asn Thr Thr Lys Ser Tyr Thr
                165                 170                 175

Leu Arg Tyr Leu Ala Ser Tyr Val Lys Lys Pro Asn Glu Asp Val Asp
            180                 185                 190

Ala Ala Gln Met Thr Ser Tyr Val Gly Phe Ser Val Val Tyr Pro
        195                 200                 205
```

*BORDETELLA BRONCHISEPTICA* VACCINE

This present application is a national phase application under 35 U.S.C. 371 of PCT/NL/93/00161, filed Jul. 28, 1993.

The present invention is concerned with a vaccine protective against *Bordetella bronchiseptica* infection in dogs, with polypeptides characteristic of *B. bronchiseptica* and with the preparation thereof using rec. DNA-technology.

The genus Bordetella is comprised of four species: *Bordetella pertussis* (*B. pertussis*), *Bordetella parapertussis* (*B. parapertussis*), *Bordetella bronchiseptica* (*B. bronchiseptica*) and *Bordetella avium* (*B. avium*). Bordetella are small gram-negative coccobacilli, obligate aerobic, often bipolar stained, and cytochrome oxidase positive. Colonies on Bordet-Gengou medium are surrounded by a zone of hemolysis except for *B. avium.*

All species of Bordetella cause very similar disease with respect to adherence, proliferation, clinical symptoms, and histopathology. Infants of man and animals are most susceptible to infection with Bordetella. Here the disease is most severe and mortality is the highest.

*B. bronchiseptica* is primarily a pathogen of laboratory, domestic and wild animals and only occasionally man. Rabbits, guinea pigs, rats, non-human primates, dogs, swine, cats, horses and foxes are often infected in epidemic. *B. bronchiseptica* most notably causes kennel cough in dogs and atrophic rhinitis in piglets. In dogs the infectious process is largely limited to the tracheobronchial tree and is characterized by proliferation on the tracheal epithelium, after adherence to the cilia. The most severe symptoms of the disease are excessive tracheal mucus accumulation, vomiting, pulmonary lesions and weight loss. Dogs have a dry, harsh hacking cough. Infection of piglets with *B. bronchiseptica* is characterized by turbinate atrophy, snout deformity, pneumonia and reduced weight gain. Although it seemed clearly established that *B. bronchiseptica* was the responsible agent of atrophic rhinitis, considerable evidence now indicates that *Pasteurella multocida* is the major phathogen with *B. bronchiseptica* possibly playing an inducing or opportunistic role. The reported carrier states, without clinical signs, are high for dogs, swine and rabbits.

Several virulence factors have been identified in Bordetellae. These include: *pertussis* toxin, filamentous hemagglutinin, fimbriae, adenylate cyclase, dermonecrotic toxin, tracheal toxin, and hemolysin. These virulence factors are not expressed in all species, for example the gene encoding *pertussis* toxin in *B. pertussis* is present as a silent gene of the chromosome of *B. parapertussis* and *B. bronchiseptica.* Besides these virulence factors there are probably more, yet unidentified, factors involved in pathogenicity of the bacteria.

Bordetella infections start at the ciliated cells of the respiratory tract. Bacterial adherence is a prerequisite for the initiation of infection since otherwise the flushing action of the cilia removes the bacteria together with other particles from the trachea. Adherence of Bordetella to ciliated cells is mediated by serologically different fimbriae and the filamentous hemagglutinin (FHA) (FHA is not found in *B. avium* however). Fimbriae are hairlike structures, composed of identical subunit proteins, extending from the bacterial cell surface. The FHA is a surface-associated protein also excreted into the extracellular environment and able to agglutinate a variety of erythrocytes. Both fimbriae and FHA expression is regulated by the bvg-locus although expression of fimbrial subunit genes, in *B. pertussis,* is also influenced by the length of a stretch of 13–15 cytosine residues in front of the fimbrial subunit genes. All virulent Bordetellae express adherence factors on their surface whereas nonvirulent strains do not. Since these adhesins are essential for the initiation of the disease, these are attractive vaccine components.

The purpose of the present invention is to provide a recombinant-DNA vaccine against *B. bronchiseptica* infection. Research has been focused on adhesion factors since prevention of adhesion, as a result of an immune response directed against adhesion factors, will prevent an infection. In *B. bronchiseptica* several serological fimbriae and FHA are responsible for adherence of the bacterium to the ciliated tracheal epithelial cells. When the host has an immune response against the adhesion factors of the microbial organism no colonization will be possible. The bacteria will be killed before any toxins are produced and no clinical symptoms will develop.

A vaccine according to the invention, preventing colonization of *B. bronchiseptica,* preferably contains as much as possible of the components necessary for adherence. A recombinant vaccine can be constructed as a subunit vaccine. It is however not known how many serologically different fimbriae are produced and what the contribution in adherence of each factor (fimbriae and FHA) is. For vaccine development it is necessary to investigate the contribution to adherence of all components separately. The proteins of interest can be used as a subunit vaccine after overproduction in a suited microbial organism.

According to the present invention three different subunit genes coding for adherence factors of *B. bronchiseptica* are isolated and characterized.

Accordingly, the present invention is concerned with a substantially pure preparation of *B. bronchiseptica* fimbrial protein or polypeptide fimbrial protein fragments (fimbrial polypeptides) having at least part of one of the amino acid sequences selected from SEQUENCE ID NO's: 2, 4 or 6.

Furthermore, the present invention is not only concerned with the fimbrial protein and polypeptides but also with DNA of SEQUENCE ID NO's: 1–3 and fragments thereof, and with polynucleotides which hybridize to said DNA and fragments thereof and which code for a polypeptide having the properties of the fimbrial protein of *B. bronchiseptica.*

The present invention is concerned also with a polynucleotide which codes for a polypeptide having the immunogenic properties of the fimbrial protein of *B. bronchiseptica* wherein at least part of the codons of the DNA of SEQUENCE ID NO's: 1, 3 or 5 or of the fragments thereof, or of the abovementioned hybridizing polynucleotide is replaced by alternative codons for the same amino acid.

The fimbrial protein and polypeptides derived thereof are able to elicit an immune response against *B. bronchiseptica.*

Small antigens often are useless as immunogens. Therefore the fimbrial protein or polypeptides may be prepared as homopolymers (a multitude of indentical fimbrial polypeptides coupled) or heteropolymers (one or more fimbrial polypeptide coupled to one or more different fimbrial polypeptides, or coupled to one or more different polypeptides characteristic of *B. bronchiseptica* or an other pathogen), or may be coupled to one or more other compounds in order to enhance immunogenicity.

According to the present invention the fimbrial polypeptide, in any of the modifications mentioned above, may be prepared by recombinant DNA techniques or may be prepared synthetically, e.g. by homogeneous or by solid state polypeptide synthesis.

The particular amino acid sequences of suitable immunogenic fimbrial polypeptides may be derived from the amino acid sequence according to SEQUENCE ID NO: 2, 4 or 6 and optionally also from the spatial configuration of the fimbrial protein. A number of methods has been developed to predict the location of immunogenically important epitopes on proteins. The outcome of the combined predictions gives a good forecast of antigenic sites.

Suitable fimbrial polypeptides may be selected from the most hydrophilic parts of the fimbrial protein, e.g. by applying the technique described by Hopp and Woods [T. P. Hopp and K. R. Woods (1981): Proc. Natl. Acad. Sci, U.S.A. 78, 3824–3828]. Another suitable method for selecting such polypeptides is described by Chou and Fasman [P. Y. Chou and G. D. Fasman (1987) Advances in Enzymology 47, 45–148].

Various additional algorithms can be used to finally predict the antigenically important regions at the *B. Bronchiseptica* fimbrial protein, such as a prediction of the flexibility of the polypeptide chain [P. A. Karplus and G. E. Schultz, 1985. Naturwissenschaften 72, 212–213], a beta-turn probability profile of the *B. bronchiseptica* fimbrial protein, according to P. Y. Chou and G. D. Fasman, 1979 [Biophys. J. 26, 367–385], the probability profiles in the 3 conformations for the sequence of *B. bronchiseptica* fimbrial proteins, according to Gascuel, O. and J. L. Golmard, 1988 [CABIOS 4, 357–365], a prediction of the secondary structure of the sequence of *B. bronchiseptica* fimbrial protein according to J. Novotny and C. Auffray, 1984 [Nucleic Acids Research 12, 243–255].

Additional information on the location of relevant epitopes can be obtained using the PEPSCAN-method, developed by Geysen and Meloen [H. M. Geysen, R. H. Meloen and S. J. Barteling (1984): Proc. Natl. Acad. Sci., 81(13); 3998–4002]. This method uses synthetic peptides of sufficient length to react in an enzyme-linked immunosorbent assay. These peptides are synthesised according to a given DNA-sequence. They are characterised by the fact that the first peptide covers amino acid nr. 1–9, the second peptide covers amino acid nr. 2–10 etc. Each peptide is tested for its reactivity with antisera or monoclonal antibodies. Reactive peptides must then represent an immunogenic epitope.

Furthermore, to identify immunoreactive epitopes (and to correlate these reactives with the physical map of the fimbrial protein) DNA fragments from the fimbrial protein gene can be expressed in suitable plasmids, such as the pEX plasmids [K. Stanley and J. P. Luzio, 1984. EMBO J. 3, 1429–1434, and J. G. Kusters, E. J. Jager and B. A. M. Van der Zeijst, 1989. Nucl. Acids Res., 17, 8007]. In this system, heterologous expression leads to the synthesis of a C-terminal extension of the cro-β-galactosidasehybrid protein. Restriction-endonuclease sites in the fimbrial protein DNA sequences can be used to obtain fragments of the fimbrial protein gene for insertion into the pEX plasmids. pEX clones synthesizing fusion proteins derived from different overlapping regions of the fimbrial protein are then used for further characterization. The pEX encoded fimbrial protein fragments are purified, fractionated by polycrylamide gel electrophoresis, and blotted to nitrocellulose membranes. These membranes are then reacted with sera from pigs or dogs immune against *B. bronchiseptica.* Only the fragments containing the immuno-reactive epitopes react with these sera. To delineate the minimal length of the epitopes, the DNA inserts of the reactive clones can be progressively shortened by Exonuclease III digestion, or by cloning synthetic oligonucleotides encoding small overlapping parts of the fimbrial protein [J. G. Kusters, E. J. Jager, G. Koch, J. A. Lenstra. W. P. A. Posthumus, R. H. Meloen and B. A. M. Van der Zeijst, 1989. J. Immunol., 143, 2692–2698]. The epitopes can then be tested for their protective effects.

According to a particular embodiment of the present invention a fimbrial-protein-specific polypeptide is produced by expression of a polynucleotide having at least part of the polynucleotides SEQUENCE ID NO: 1, 3 or 5 forming part of a recombinant polynucleotide. The recombinant polynucleotide preferably may be based on a vector with a *B. bronchiseptica*-specific polynucleotide fragment inserted therein. Suitable vectors are plasmids, bacteriophages, cosmids, viruses, minichromosomes or stably integrating vectors; the latter in particular for plant or animal cells. Generally these vectors have the property of autonomous replication except for the stably integrating vectors which insert themselves in the genetic material of the host cell and replicate with the host's genetic material. Suitable host cells may be either prokaryotic or eukaryotic, such as bacteria, yeasts, mycoplasms, algae, plant cells or animal cells; the plant cells or animal cells may be cultivated in vitro or may form part of an intact plant or animal, respectively. The recombinant polynucleotide may contain as an insert a complete polynucleotide coding for the fimbrial protein or a fragment thereof. The insert may comprise a single coding sequence, or multiple copies of the same coding sequence, or a hybrid polynucleotide containing at least one fimbrial protein coding sequence and at least one second sequence such as a different part of the fimbrial protein coding sequence or a polynucleotide coding for a protein characteristic of an other pathogen or for an inert protein functioning as a carrier for at least one small fimbrial-polypeptide.

A specific case of the above embodiment is concerned with recombinant polynucleotides with viral vectors, directly useful as so-called vector vaccines. The viruses applicable for this purpose should have the ability to replicate in the animals to be immunized, i.e. in dogs and/or swines. These viruses, furthermore, should possess a genomic region suitable for insertion of a foreign gene (e.g. coding for the *B. bronchiseptica*-fimbrial protein or polypeptide) which is also to be expressed in the vaccinated animal. Suitable viruses for this purpose are for example enteral viruses such as certain adeno viruses.

As was indicated above, the proteins and polypeptides, and the recombinant polynucleotides according to the invention are useful in the preparation of vaccines. Hence, these vaccines also form part of the invention.

A particular application of the present invention is concerned with bacterial vector vaccines. Herein Bacteria capable of colonizing dogs and/or swines are transformed in order to enable them to express a fimbrial protein or fimbrial polypeptide in such a way that it will lead to an immunogenic response against *B. bronchiseptica.* Suitable bacteria for this purpose are e.g. Salmonella bacteria.

A vaccine according to the invention may also contain auxiliary vaccine constituents, such as carriers, buffers, stabilizers, solubilizers, adjuvants and preservatives. Advantageously these vaccines are freeze-dried products which are reconstituted by the addition of a suitable liquid (water, buffer) prior to application.

The vaccine can be applied e.g. orally, intranasally or intramuscularly.

The vaccine may additionally contain other immunogens for the animals to be immunized (dogs and swines), such as immunogenic material characteristic of viruses such as pseudorabies virus, influenza virus, transmissible gastroenteritis virus, parvo virus, porcine endemic diarhoea virus, hog cholera virus, or immunogenic material characteristic of mycoplasma, such as *Mycoplasma hyopneumoniae* and *Mycoplasma lyorhinis,* or immunogenic material charactereristic of bacteria, such as *Escherichia coli,* Leptospira, *Actinobacillus pleuropneumoniae, Pasteurella multocida,* Streptococcussuis, *Treponema hyodysenteriae.*

BRIEF DESCRIPTION OF THE DRAWINGS

FIG. 1 shows a construct used for gene replacement in *B. bronchiseptica;*

FIG. 2 shows that the fimX gene is expressed in high levels in *B. bronchiseptica;*

Figure 3:
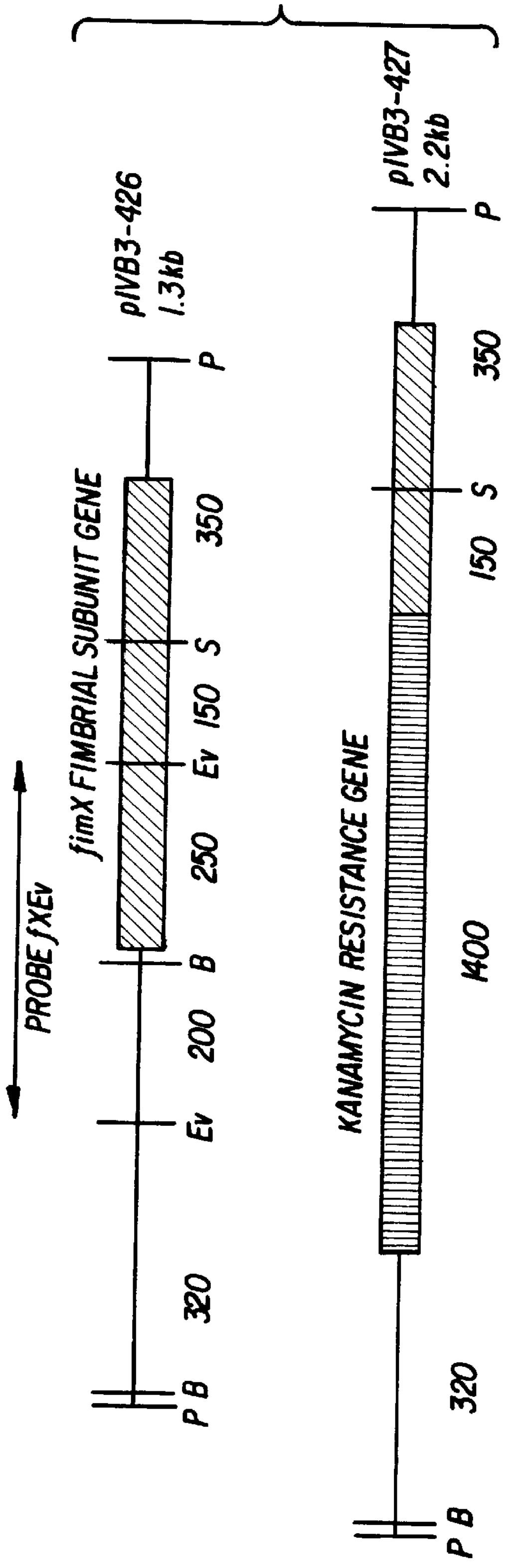
FIG. 3 shows inter alia the hybridization of digested chromosomal DNA of *B. bronchiseptica* with probe fxEv.

The invention is illustrated by the following working Examples.

EXAMPLE 1

Characterization of the Fimx Gene

Materials and Methods

Bacterial strains, media and growth conditions

All bacterial strains used are listed in Table 1.

TABLE 1

| STRAIN | SOURCE | OBTAINED FROM |
|---|---|---|
| *Bordetella bronchiseptica* strain no. 401 | clinical isolate dog (USA) no. 685 | J. M. Musser, New York |
| *Bordetella bronchiseptica* strain no. BbfX | fimX negative strain: derivative of no. 401 | P. H. M. Savelkoul, Utrecht |
| *Bordetella pertussis* strain Welcome 28 | clinical isolate human | F. R. Mooi, Bilthoven |
| *Bordetella avium* strain no. 182 | clinical isolate turkey; (FRG) no. 383–78 (10) | K.-H. Hinz, Hannover |
| *Escherichia coli* strain PC2495 K12 | hsdS. recA derivative of JM 101 | Netherlands Culture Collections of Micro-organisms |

All Bordetella strains were grown on Bordet-Gengou agar (Difco Laboratories, Detroit. Mich.) supplemented with 1% glycerol and 20% defibrinated sheep blood or in Tryptose Phosphate Broth (TPB) (Difco Laboratories. Detroit. Mich.). To suppress the expression of virulence genes, the media were supplemented with 20 mmol/l $MgSO_4$. *B. bronchiseptica* strain 401 is used for DNA preparations. *Escherichia coli* strain PC2495 was used for the propagation of the vector Bluescript (Stratagene) and its derivatives. Strain PC2495 was grown on Lureano-Bertoni (LB) bouillon or LB agar. Ampicillin (50–100 μg/ml resp.), 50 μg/ml 5-bromo-4-chloro-3-indolyl-β-D-galactopyranoside (X-gal) and 20 μg/ml isopropyl-β-D-thiogalactopyranoside (IPTG) was used for identification of plasmid containing strains carrying a DNA insert. All bacterial cultures were grown at 37° C. for 16–24 hours.

Recombinant DNA Methods

Chromosomal DNA was isolated from Bordetella strains as described by Maniatis et al. [T. Maniatis, E. F. Fritsch and J. Sambrook 1982. Molecular cloning: A Laboratory Manual. Cold Spring Harbor, N.Y.: Cold Spring Harbor Laboratory Press]. After digestion, electrophoresis of DNA was performed in 1% agarose gels in TAE buffer (40 mmol/l Tris-acetate, 2 mmol/l EDTA) containing 1 μg/ml ethidium bromide. The Geneclean kit was used to isolate DNA fragments from agarose gels (Bio Inc. 101 Corp., La Jolla). End-labeling of oligonucleotides was performed with [γ-$^{32}$P]dATP using T4 polynucleotide kinase [Maniatis et al.]. Hybridization was performed in 5×SSPE, 5×Denhardt's solution, 0.1% SDS and 100 μg/ml herring sperm DNA at 55° C. Blots were washed with 5×SSPE and 0.1% SDS at 55° C.

Southern Blot Analysis

Chromosomal DNA of the *B. bronchiseptica* strain 401 was purified and digested with several restriction enzymes. Fragments were separated by electrophoresis, transformed to a nylon membrane and hybridized with a DNA probe derived from the fimX fimbrial subunit gene of *B. pertussis.* DNA fragments of interest, identified from hybridization signals, were isolated by the Gene Clean kit (Bio Inc. 101 Corp., La Jolla). After ligation into the Bluescript vector (Stratagene), the chromosomal DNA fragments were transformed to *Escherichia coli,* strain PC2495, according to the $CaCl_2$ method [Dagert, M., and Ehrlich, S. D. 1979. Prolonged incubation in calcium chloride improves the competence of *Escherichia coli* cells. Gene 6:23–28]. Positive colonies were identified after hybridization.

Nucleotide Sequence Determination

Plasmid were isolated according to the alkaline lysis method [H. C. Birnboim and J. A. Doly 1979. A rapid alkaline extraction procedure for screening recombinant plasmid DNA. Nucleic Acids Res. 7:1513–1523]. The nucleotide sequence of the cloned inserts was determined by the dideoxy chain termination method [F. Sanger, S. Nicklen, A. R. Coulson 1977. DNA sequencing with chain-terminating inhibitors. Proc. Natl. Acad. Sci. U.S.A. 74:5463–5467]using the T7 polymerase sequencing kit (Amersham). Analysis of the DNA sequence data was performed with the PC/Gene software (release 6.5, Genofit, Heidelberg S. A., Geneva. Switzerland).

Partial Fimbriae Purification

*B. Bronchiseptica* strain 401 was grown on Tryptose Phosphate Agar (Difco Laboratories, Detroit. Mich.). The bacteria were washed in phosphate buffered saline (PBS). The bacterial pellet was suspended in 15 ml phosphate buffered saline supplemented with 4 mol/l ureum. This suspension was placed at 40° C. for 30 min. The bacteria were removed from the suspension by centrifugation at 20,000 rpm (Beckman, JA20 rotor) during 10 min. Fimbriae were isolated from the supernatant after centrifugation at 40,000 rpm (Beckman ultracentrifuge, Ti60 rotor) during 16 hours. The pellet was then suspended in 5 ml phosphate buffered saline. Protein concentration was determined with the Bicinchoninic acid (BCA) assay (Pierce Chemical Company, U.S.A.). Protein analysis was performed on a 15% SDS-polyacrylamide gel electrophoresis system.

Results

Sequence Analysis and Alignment

A BamHI-EcoRI DNA fragment derived from the fimX gene of *B. pertussis* was used as a probe to identify *B. bronchiseptica* chromosomal DNA fragments containing fim genes. A 1.3 kb PstI DNA fragment from *B. bronchiseptica,* hybridizing to the fimX probe, was isolated and sequenced. On this fragment the complete fimX gene, including promotor sequences in front of the gene, was located (SEQUENCE ID NO: 1).

*E. coli* PC 2495 bacteria containing the plasmid plVB 3-420 containing the complete fimX gene was deposited at the Centraalbureau voor Schimmelcultures at Baarn, the Netherlands on Aug. 13, 1992, under deposit number CBS 364.92.

Expression of the fimX gene of *B. bronchiseptica*

To identify the fimX product, a deletion mutant strain, unable to express the fimX gene, was constructed. This mutant strain was constructed by gene replacement. To this end a central EcoRV fragment of the *B. bronchiseptica* fimX gene was replaced by a kanamycin gene and cloned in the Bluescript vector. This construct was used for gene replacement in *B. bronchiseptica* (FIG. 1). A kanamycin resistant mutant strain was identified. The strain did not hybridize with the EcoRV fragment anymore. From this mutant strain partially purified fimbriae were prepared. This purification of fimbriae from the fimX-negative strain compared to the wildtype strain clearly showes that the fimX gene is expressed at a high level in *B. bronchiseptica* (FIG. 2).

EXAMPLE 2

Characterization of the fim2 and fim3 fimbrial subunit gene of *Bordetella bronchiseptica*

Materials and Methods

Bacterial strains, plasmids and growth conditions

The wildtype *B. bronchiseptica* strain used was isolated from dogs, suffering from kennel cough. This strain was obtained from Dr. J. M. Musser (strain no. 685) and designated no. 401. This strain was grown in Tryptose phosphate broth or agar (Difco laboratories, Detroit, Mich.). The *B. pertussis* strain Wellcome 28 [A. Robinson, L. A. E. Ashworth, A. Baskerville, and L. I. Irons. 1085. Proceedings of the 4th International Symposium on *pertussis,* Geneva, 1984. Dev. Biol. Stand. 61:165–172]was grown on Bordet Gengou agar (Difco Laboratories, Detroit, Mich.). For non-virulent *B. bronchiseptica* the growth media were supplemented with 20 mmol/l $MgSO_4$,. *E. coli* K12 strain PC2495 was used as host for the cloning vector pBluescript. The *E. coli* strain was grown on LB agar or LB bouillon supplemented with 100 $\mu$g/ml amp.; 50 $\mu$g/ml X-Gal and 20 $\mu$g/ml IPTG for identification of recombinant strains containing an cloned DNA fragment. All bacterial cultures were grown at 37° C. for 16–48 hours.

DNA isolation and nucleotide sequence determination

Isolation of chromosomal DNA was carried out according to Maniatis et al. Plasmid isolation was carried out by the method of Birnboim and Doly. Chromosomal DNA fragments were isolated from TAE (40 mmol/l Tris-acetate, 2 mmol/l EDTA) agarose gels using the Gene Clean Kit (Bio Inc. 101 Corp., La Jolla). DNA fragments were ligated in pBluescript KS M13+and M13–(Stratagene. La Jolla, Calif.) for all cloning purposes. Nucleotide sequence determination was carried out with the T7 polymerase sequencing kit (Amersham) by the dideoxy chain termination method of Sanger et al. PC/Gene computing software (release 6.5, Genofit, Heidelberg S. A., Geneva, Switzerland) was used for analyzing DNA sequence data. Restriction enzymes and T4 DNA ligase were purchased from Pharmacia and were used according to the instructions of the manufacturer. Plasmids were transformed to the *E. coli* strain PC2495 by the $CaCl_2$ method of Dagert and Ehrlich.

Southern blotting

Southern blotting was carried out according to Maniatis et al.

SDS-Polyacrylamide Gel Electrophoresis and Immunological Techniques

For SDS-PAGE and Western blot analysis equal amounts of bacteria were used. Bacteria were harvested in Phosphate Buffered Saline (PBS) buffer and diluted until $OD_{600}$=1.0. From this suspension 50 $\mu$l was lysed in 20 $\mu$l Laemmli buffer and electrophoresed on 15% polyacrylamide gels as described by Laemmli [Laemmmli, U.K. 1970. Cleavage of structural proteins during the assembly of the head of bacteriophage T4.Nature 227:680–685]. Transfer of the proteins to nitrocellulose was essentially carried out as described by van Embden et al.[J. D. A. van Embden, H. J. van der Donk, H. J. van Eijk, H. G. van der Heide, J. A. de Jong, M. F. van Olderen, A. D. Osterhaus, L. M. Schouls. 1983. Molecular cloning and expression of *Treponema pallidum* DNA in *Escherichia coli* K12.*Infect. Immun.* 42:187–196]. Polyclonal antibodies, raised against SDS-denatured serotype 2 or 3 fimbrial subunit proteins from *B. pertussis,* were used for detection of *B. bronchiseptica* fimbrial subunit proteins.

Fim2 and fim3 specific monoclonal antibodies, raised against *B. pertussis,* were used in an ELISA on flat bottom microtiter plates coated with whole bacteria ($OD_{600}$=0.1, 1:10 diluted in 15 mmol/l $Na_2CO_3$ , 35 mmol/l $NaCO_3$, pH 9.6). Bound goat anti-mouse IgG-peroxidase conjugate (Nordic) was determined with 2,2'-azino-bis(3-ethylbenzthialzolin-6-sulfonic acid (ABTS) (Sigma), Absorbance was measured at 405 nm.

Electron Microscopy

For electron microscopy a *B. bronchiseptica* culture was diluted in PBS buffer. Pilioform coated copper grids were placed on 50 $\mu$l bacterial suspension for 5 min. Grids were washed 2 times in $H_2O$. Staining was performed during 2 min. in 1% TPA (Tungstophosphoric acid, Merck). The grids were examined in a Philips EM 201 electron microscope.

Results

Nucleotide Sequence of the Fim2 and Fim3 Fimbrial Subunit Genes

The *B. bronchiseptica* fim2 and fim3 subunit genes could be identified on the basis of their homology with the *B. pertussis* fim2 and fim3 genes, respectively. An Accl-Pstl DNA fragment of 1000 bp was used as a probe for the fim2 gene [I. Livey, C. J. Duggleby, and A. Robinson. 1987. Cloning and nucleotide sequence analysis of the serotype 2 fimbrial subunit gene of *Bordetella pertussis.* Mol. Microb. 1:203–209]. A SalI DNA fragment of 900 bp was used as a probe for the fim3 gene [Mooi, F. R., A. ter Avest, and H. G. J. van der Heide. 1990. Structure of the Bordetella pertussis gene coding for the serotype 3 fimbrial subunit. FEMS Microb. Lett. 66:327–332]. Hybridization of chromosomal DNA from *B. bronchiseptica,* digested with the restriction endonuclease PstI, yielded several positive signals with both probes due to the homology between the two probes. Two regions of DNA fragments were isolated from *B. bronchiseptica* chromosomal DNA giving the strongest signal with either the fim2 or the fim3 probe. These PstI DNA fragments of about 2.3 kb and 2.8 kb respectively were cloned into the Bluescript vector. After transformation and colony lifting two clones were identified by hybridization with either of the fim probes. One clone, with an insert of 2.3 kb, encoded the fim2 (pIVB3-402) gene. The other clone, with an insert of 2.8 kb, encoded the fim3 (pIVB3-430) gene of *B. bronchiseptica.* The nucleotide sequence of both genes was determined and are represented as SEQUENCE ID NO 3 (fim2) and SEQUENCE ID NO 5 (fim3), respectively. The *E. coli* bacteria PC 2495 (pIVB3-402) and PC 2495 (pIVB3-430) were deposited at the Centraalbureau voor Schimmelcultures at Baarn, The Netherlands Aug. 13, 1992 under the No's CBS 362.92 and CBS 361.92, respectively.

EXAMPLE 3

Construction of two *Bordetella bronchiseptica* Strains that are Deficient in the Production of one Type of Fimbriae

*Bordetella bronchiseptica* strains deficient in the production of FimX fimbriae ($BbfX^-$) or Fim2 fimbriae ($Bbf2^-$) have been constructed. This was obtained by gene replacement with the disrupted genes after homologous recombination. The disrupted genes were transformed to *B. bronchiseptica* by electroporation. The deletion in the fimbrial subunit genes was constructed by replacement of an EcoRV fragment in the wild-type genes with a kanamycin resistance gene.

Materials and Methods

Bacterial strains, plasmids and growth conditions

The wildtype *B. bronchiseptica* strain no. 401 was used in all experiments. The bacterium was obtained from Dr. J. M. Musser (strain no. 685). This strain was grown on tryptose phosphate agar (TPA) (Difco Laboratories) or on Bordet Gengou (BG) agar (Difco Laboratories) supplemented with 15% fresh sheep erythrocytes, at 37° C. for 24–48 hrs. For cloning purposes *Escherichia coli* K12 strain PC2495 was used with the Bluescript KS and SK plasmid (Stratagene). *E. coli* PC2495 was grown on Luria Bertoni agar with the proper antibiotics during 16 hrs. at 37° C. For ampicillin and/or kanamycin a concentration of 100 μg/ml was used.

Recombinant DNA Techniques

Cloning procedures were carried out as described by Maniatis et al. Each fimbrial subunit gene, including adjacent sequences, was cloned in the Bluescript vector. These vectors were isolated by the alkaline extraction method of Birnboim and Doly. A DNA fragment within a subunit gene was replaced by a kanamycin resistance gene [A. Labigne-Roussel, J. Harel, and L. Tompkins. 1987. Gene transfer from *Escherichia coli* to Campylobacter species: Development of shuttle vectors for genetic analysis of *Campylobacter jejuni.* J. Bacteriol. 169:5320–5323]. This latter construct was used in electroporation experiments.

Electroporation Experiments

Electroporation was performed essentially as described by Miller et al. [J. F. Miller, W. J. Dower, and L. S. Tompkins. 1988. High-voltage electroporation of bacteria: Genetic transformation of *Campylobacter jejuni* with plasmid DNA. Proc. Natl. Acad. Sci. U.S.A. 85:856–860]. The wildtype *B. bronchiseptica* strain 401 was grown on BG agar during 16 hrs. The cells were harvested in 1 ml of a 15% glycerol-272 mmol/l sucrose solution (GlySuc) (0° C.), washed and resuspended in 400 μl GlySuc. From this suspension aliquots of 50 μl were frozen at −80° C. These aliqouts were used in electroporation experiments to transform *B. bronchiseptica* with 1–3 μg DNA, dissolved in aqua dest. The electroporation conditions used are: 0.7 kV, 25 μF and 600Ω (Biorad Gene Pulser, using 0.56 mm gap cuvettes from Biotechnologies and Experimental Research Inc., San Diego, Calif.). Time constants measured were between 3.5–7 ms. Cells were recovered in 1 ml. tryptose phosphate broth (Difco Laboratories) during 90 min. at 37° C. and plated on TPA (Difco Laboratories) containing 100 μg/ml kanamycin. Screening of recombinant strains was carried out by Southern blotting on chromosomal DNA preparations.

Chromosomal DNA Purification and Southern Blot Analysis

Figure 4:
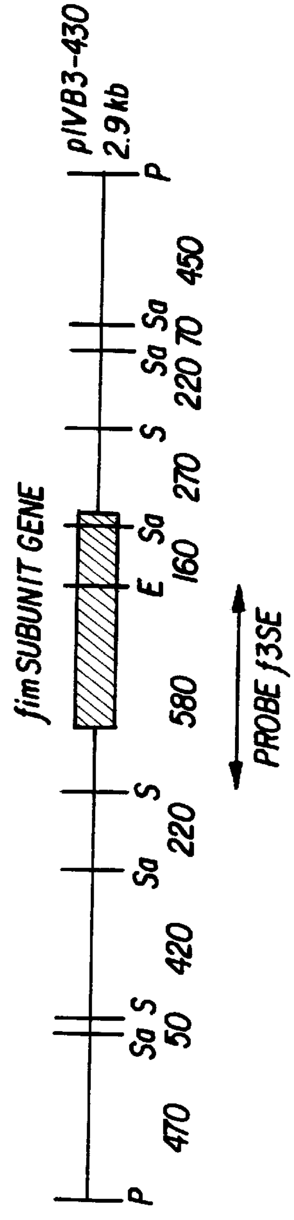
FIG. 4 shows inter alia the hybridization of digested chromosomal DNA of *B. bronchiseptica* probe f3SE.
Figure 5:
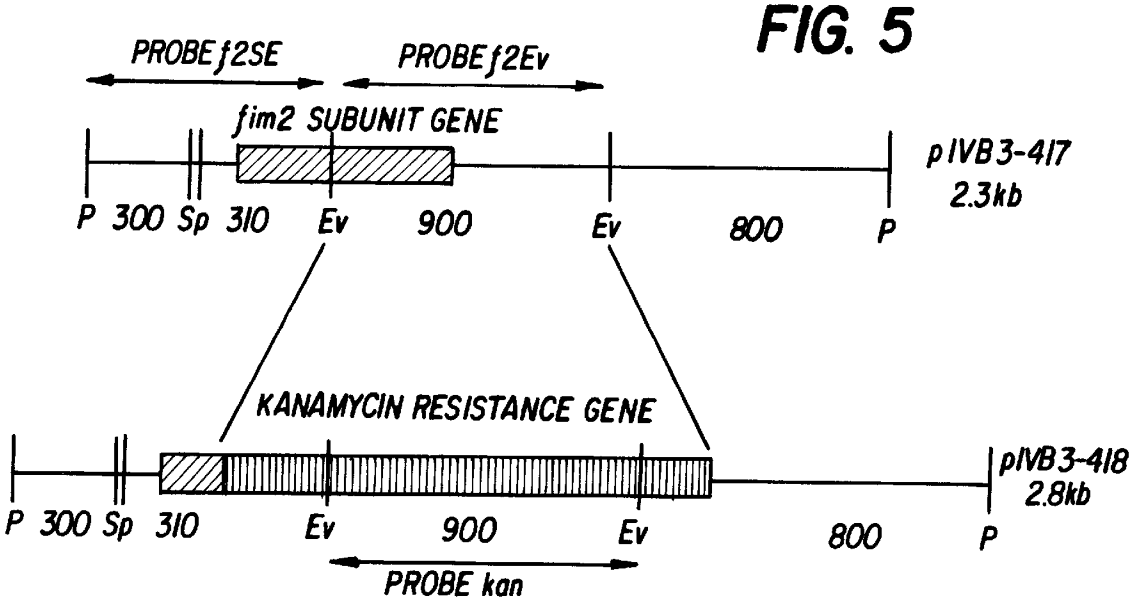
FIG. 5 shows ligation of the kanamycin gene in plVB3-417 yielded the clone pIVB3-418 and hybridization of the new plasmid with f2Ev, kan and f2SE.

Chromosomal DNA was purified according to maniatis et al. Southern blot analysis was carried out as previously described DNA Probes used in Hybridization Experiments For hybridization experiments concerning the fimX gene two probes were used designated fXEv and f3SE. A 450 bp DNA fragment, used as probe fxEv, was isolated from digestion of pIVB3-426 with the restriction endonuclease EcoRV (FIG. 3). The 580 bp DNA fragment of probe f3SE was obtained after digestion of pIVB3-430 with the restriction endonucleases SphI and EcoRI (FIG. 4). For hybridization experiments concerning the fim2 gene three probes were used designated f2Ev, kana and f2PE (FIG. 5). Probe f2Ev was a 900 bp EcoRV DNA fragment isolated from pIVB3-417, probe kana was a 900 bp EcoRV DNA fragment within the kanamycin gene and probe f2PE was a 610 bp PstI-EcoRV DNA fragment of pIVB3-417.

Results

Two plasmids with DNA fragments containing either the fimX or the fim2 fimbrial subunit gene were used to transform wildtype *B. bronchiseptica* bacteria by electroporation. The genes of both subunits were disrupted by replacement of an EcoRV DNA fragment with a kanamycin resistance gene. Before this could be done a third EcoRV site, present in the polylinker of the Bluescript vector, had to be removed. This was done by subcloning the DNA fragments into an EcoRV Bluescript vector resulting in pIVB3-426 for fimX and pIVB3-417 for fim2 (FIG. 3, 5). Both clones were then digested with the restriction endonuclease EcoRV. With this digestion a fragment of 450 bp was removed from the fimX gene clone (pIVB3-426) including the 5' promotor sequences (FIG. 3). After the EcoRV fragment was removed the vector with the remaining DNA sequences was isolated and a 1.4 kb SmaI-HincII DNA fragment containing a kanamycin resistance gene was cloned into the EcoRV sites. Transformation to *E. coli* PC2495 followed by plasmid isolation yielded the clone pIVB3-427 (FIG. 3). The same strategy was followed for the fim2 fimbrial subunit gene. Digestion of clone pIVB3-417 with the restriction endonuclease EcoRV (FIG. 5) removed a 900 bp DNA fragment towards the 3' part of the gene together with adjacent sequences. Ligation of the kanamycin resistance gene in this construct yielded the clone pIVB3-418 (FIG. 5).

Figure 6:
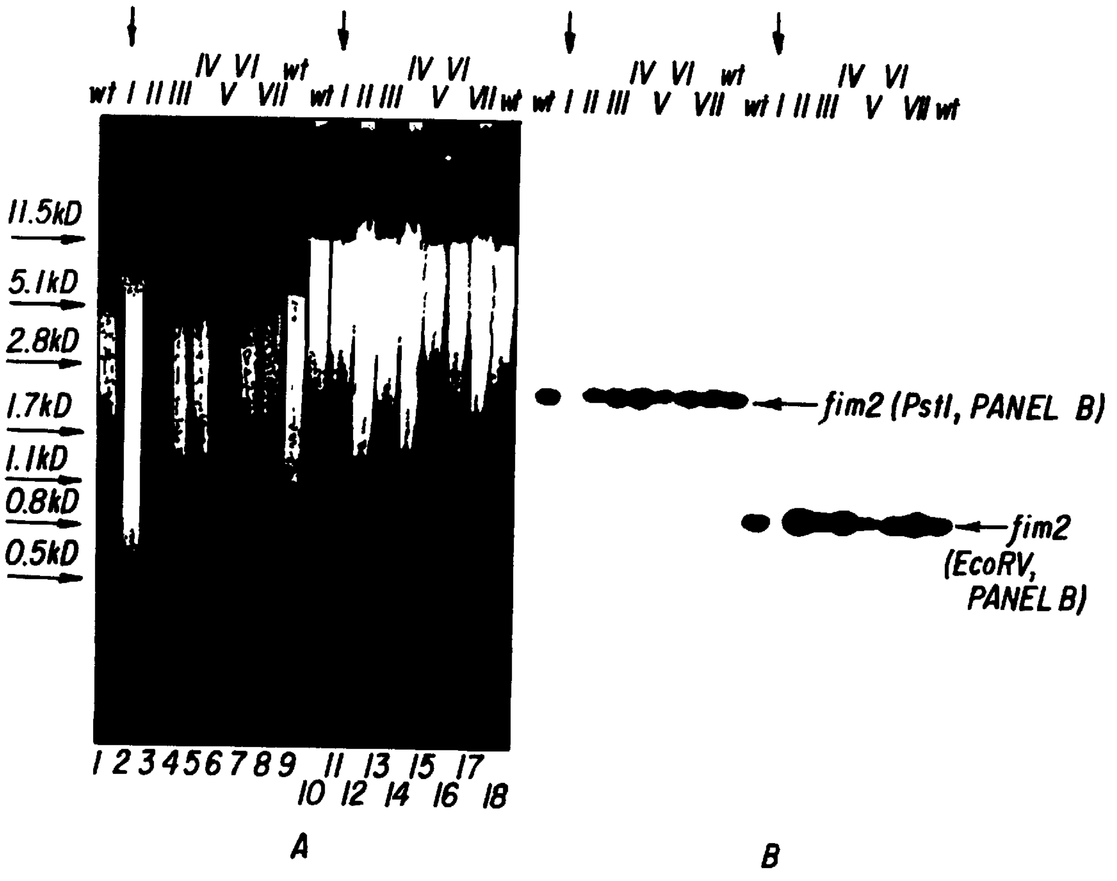
FIGS. 6A and 6B show the hybridization patterns of recombinant strains.
FIG. 6C shows inter alia hybridization signals with DNA fragments containing the fim3 and fim2 gene.
Figure 7:
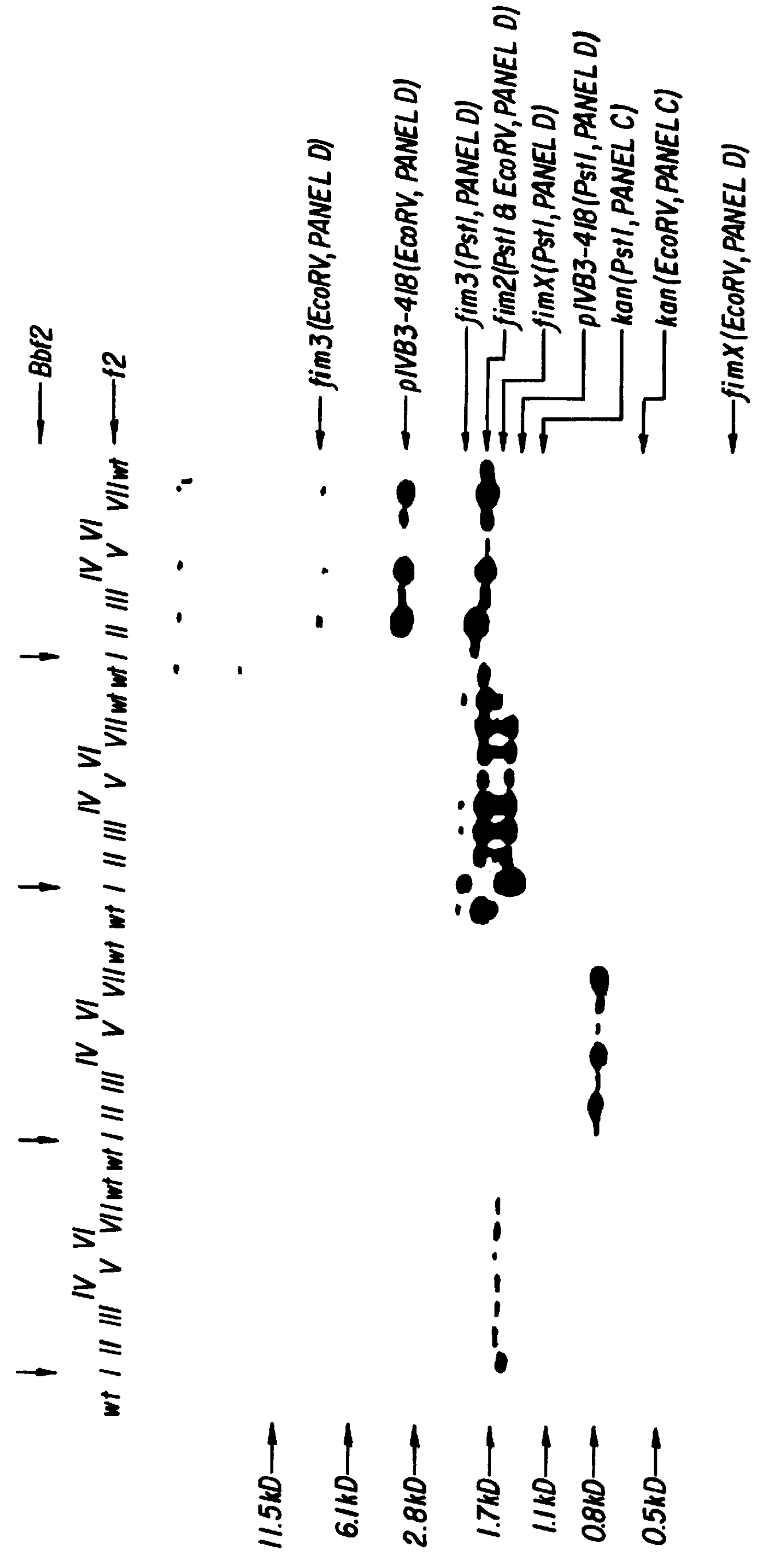
FIGS. 7A and 7B show the hybridization patterns of recombinant strains.
FIG. 7C shows the presence of the kanamycin gene in all isolated fim2 recombinant strains.
FIG. 7D shows gene replacement in only strain BbF2.

Both plasmids (pIVB3-427 and pIVB3-418) were isolated and separately used in electroporation experiments to transform *B. bronchiseptica.* After each electroporation experiment up to $10^2$ kanamycin resistant *B. bronchiseptica* colonies were observed. After electroporation with plasmid pIVB3-427 (partial fimX fimbrial subunit gene), 4 colonies were analyzed (fX I–IV). After electroporation with plasmid pIVB3-418 (partial fim2 fimbrial subunit gene), 7 colonies were analyzed (f2 I–VII). Chromosomal DNA was isolated from these kanamycin resistant *B. bronchiseptica* strains and digested with the PstI and EcoRV restriction endonucleases respectively. A Southern hybridization was performed with the digested chromosomal DNA, isolated from the kanamycin resistant strains and the wildtype *B. bronchiseptica* strain. The digested chromosomal DNA of the 4 strains isolated after the electroporation with pIVB3-427 was hybridized with probes fXEv and f3SE respectively (FIGS. 3, 4). The digested chromosomal DNA of the 7 strains isolated after electroporation with plasmid pIVB3-418 was hybridized with probes f2Ev, kan and f2SE respectively (FIG. 5). From the hybridization patterns with probes fXEv and f2Ev it was clear that recombinant strains, missing either a part of the fimX (FIGS. 6A, 6B) or the fim2 (FIGS. 7A, 7B) fimbrial subunit gene, were isolated. From hybridization experiments with the kanamycin gene as a probe it was demonstrated for the fim2 gene that all strains isolated (f2 I–VII) did contain the kanamycin gene (FIG. 7C).

Since the kanamycin gene was present in all fim2 recombinant strains gene replacement could have occured within one of the other fimbrial subunit genes due to homologies among the subunit genes. To determine whether this was the case hybridization experiments were carried out under low stringency conditions whereby crosshybridization could be observed using probes derived from the other subunit genes. Hybridization experiments on the fimX kanamycin resistant *B. bronchiseptica* strains (fX I–IV) with the f3SE probe (fim3 subunit gene) demonstrated that gene replacement in the fimbrial subunit gene occurred only within strain BbFX⁻. In this strain as well as the other recombinant strains (fX II–IV) hybridization signals with DNA fragments containing the fim3 and fim2 genes were present (FIG. 6C). Since these latter signals were the same as in the wildtype *B. bronchiseptica* no recombination in one of the other subunit genes has occured (FIG. 6C). Hybridization of the fim2 mutant strains with the f2PE probe showed that gene replacement in the fim2 gene only has occurred within strain BbF2⁻ (FIG. 7D). With the use of this probe hybridization signals with all three subunit genes are observed. Since the PstI-EcoRV fragment (probe f2PE) is present within pIVB3-418, used in the electroporation, a fourth hybridization signal can be observed in the recombinant strains (f2 II–VII). This indicates that the plasmid pIVB3-418 may still be present in the kanamycin resistant strains. Probably recombination has occured elsewhere in the chromosome at an unidentified location outsite a fimbrial subunit gene.

EXAMPLE 4

Vaccination Challenge Experiment with *Bordetella bronchiseptica* Mutants BBFX⁻ and BBF2⁻ in Mouse

Materials and Methods

Three groups of 80 mice each (6 weeks old Female BALB/C mice) were intranasally infected with wildtype *B. bronchiseptica,* BbfX⁻ and Bbf2⁻ (the latter two prepared according to EXAMPLE 2), respectively (2×10e7 cfu each). The number of viable bacteria in the respiratory tract of 8 mice was determined at specified time intervals (0, 1, 3, 7, 11 and 36 days). Of each mouse the nasopharynx, nose, trachea and lungs were examined for the presence of viable *B. bronchiseptica.* Mice were sacrificed by a barbiturate injection approximately 1 h after infection (designated as day 0) and on various days thereafter. The lungs and trachea were removed and homogenized in PBS with tisue grinders. Noseswabs were taken with cat gut. The cat gut was placed in 0.5 ml PBS and vortexed for 5 min. The nasopharynx was rinsed with PBS-until 5 droplets (approximately 0.5 ml) were collected. Dilutions of all homogenates and the droplets of the nasopharynx were plated on Tryptose Phosphate Agar and CFU were counted after 2 days of incubation.

52 days after vaccination, the groups vaccinated with BbfX⁻ or Bbf2⁻ and a nonvaccinated control group were challenged with a virulent *B. bronchiseptica* strain. Colonization of the respiratory tract was measured at day 0, 1, 4 and 14 after challenge.

Results

The results on colonization of the upper respiratory tract of both mutant strains with the wild type strain is compared. There is no difference in colonization of the various organs of the upper respiratory tract after challenge with the BbfX⁻ or Bbf2⁻ mutant strain compared with the wild type strain.

At day 36 mice of the BbfX⁻ and Bbf2⁻ groups were screened for the presence of Bordetella. Lungs and trachea were free of Bordetella whereas small amounts of Bordetella were still present in nose and nasopharynx.

At day 52 after vaccination, the mice which were vaccinated with BbfX⁻ and Bbf2⁻ mutants and a control group were challenged with a virulent *B. bronchiseptica* strain. Colonization of the nasopharynx with the virulent *B. bronchiseptica* strain could not be prevented in both vaccinated groups.

Lung and trachea colonization of wildtype strain in the vaccinated groups could only be demonstrated one hour after challenge, whereas the control group was severely colonized.

The colonization of the nose of the mice vaccinated with the mutant strain could only be detected at day 0 and in some mice at day 1, whereas the nose of the mice of the control group were heavily colonized.

We claim:

1. An isolated polynucleotide coding for a polypeptide having the immunogenic characteristics of a fimbrial protein of *B. bronchiseptica* and having a nucleotide sequence selected from the group consisting of SEQUENCE ID NO: 3, and SEQUENCE ID No; 5.

2. An isolated polynucleotide capable of expressing a polypeptide having the immunogenic characteristics of a fimbrial protein of *B. bronchiseptica,* according to claim 1, further comprising a suitable vector functionally linked thereto.

3. A *B. bronchiseptica* strain containing an isolated polynucleotide according to claim 2 and capable of producing a polypeptide having the immunogenic characteristics of a fimbrial protein of *B. bronchiseptica.*

4. A vaccine for generating an immunologic response to *B. bronchiseptica* infection in susceptible animals containing an inert carrier as well as a *B. bronchiseptica* strain according to claim 3.

5. A method for generating an immunologic response to a *B. bronchiseptica* in susceptible animals comprising administration of a vaccine containing a *B. bronchiseptica* strain according to claim 4 to said susceptible animals.

* * * * *